(12) United States Patent
Yoshizawa et al.

(10) Patent No.: US 6,392,105 B1
(45) Date of Patent: *May 21, 2002

(54) PROCESS FOR PRODUCTION OF FLUOROALCOHOL

(75) Inventors: Toru Yoshizawa; Shoji Takaki; Takashi Yasuhara; Yasunori Yokoyama, all of Settsu (JP)

(73) Assignee: Daikin Industries, Ltd., Osaka-fu (JP)

(*) Notice: Subject to any disclaimer, the term of this patent is extended or adjusted under 35 U.S.C. 154(b) by 0 days.

This patent is subject to a terminal disclaimer.

(21) Appl. No.: 09/388,384

(22) Filed: Sep. 1, 1999

(30) Foreign Application Priority Data

Dec. 28, 1998 (JP) .............................. 10-373972
Feb. 25, 1999 (JP) .............................. 11-048446

(51) Int. Cl.[7] ........................ C07C 31/34; C07C 29/00; C07C 29/80
(52) U.S. Cl. ...................... 568/842; 568/904; 568/913
(58) Field of Search ................. 568/842, 904, 568/913

(56) References Cited

U.S. PATENT DOCUMENTS

| | | | |
|---|---|---|---|
| 2,559,628 A | | 7/1951 | Joyce, Jr. |
| 4,346,250 A | | 8/1982 | Satokawa et al. ............ 568/842 |
| 5,023,377 A | * | 6/1991 | Desmarteau et al. ........ 564/301 |

FOREIGN PATENT DOCUMENTS

| | | |
|---|---|---|
| CZ | 244792 | 11/1985 |
| CZ | 268247 | 7/1989 |
| EP | 0398154 | 11/1990 |
| EP | 0 968 989 A2 | 1/2000 |
| JP | 2-188540 | 7/1990 |
| JP | 5-16529 | 1/1993 |
| JP | 4-8585 | 10/1993 |
| JP | 5-225619 | 11/1993 |
| JP | 5-258346 | 12/1993 |
| JP | 5-339183 | 12/1993 |
| JP | 7-137448 A | 5/1995 |
| JP | 8-291091 A | 11/1996 |

OTHER PUBLICATIONS

Chemistry of Organic Fluorine Compounds, Milos Hudlicky ed. (1976), pp. 340–341 (attached to Opposition No. 2000–73767 01).

J. Am. Chem. Soc., vol. 83 (1961), pp. 3142–3147 (attached to Opposition No. 2000–73767 02).

Kosower et al., "The Effect of Solvent on Spectra v. the Low Intensity . . . ", Journal of the American Chemical Society, vol. 83, 1961, pp. 3142–3147.

* cited by examiner

Primary Examiner—Peter O'Sullivan
(74) Attorney, Agent, or Firm—Larson & Taylor PLC

(57) ABSTRACT

The invention provide a method for producing a fluoroalcohol of the following formula (1):

$$H(CFR^1CF_2)_nCH_2OH \qquad (1)$$

(wherein $R^1$ represents F or $CF_3$, when n=1; $R^1$ represents F, when n=2) comprising reacting methanol with tetrafluoroethylene or hexafluoropropylene in the presence of a free radical source, wherein the reaction mixture is subjected to distillation either in the presence of a base or after contact of said reaction mixture with a base.

20 Claims, No Drawings

PROCESS FOR PRODUCTION OF FLUOROALCOHOL

TECHNICAL FIELD

The invention relates to a process for producing a fluoroalcohol of the general formula (1):

$$H(CFR^1CF_2)_nCH_2OH \quad (1)$$

(wherein $R^1$ represents F or $CF_3$, when n=1; $R^1$ represents F, when n=2), said fluoroalcohol which is substantially impurity-free, and use of said fluoroalcohol for the manufacture of an information recording medium comprising a substrate and as built thereon a recording layer adapted for laser writing and/or reading.

BACKGROUND ART

Regarding the technology of producing $H(CF_2CF_2)_nCH_2OH$ (n=1, 2), it is disclosed in Japanese Unexamined Patent Publication 154707/1979 and U.S. Pat. No. 2,559,628 that a mixture of telomers, i.e., $H(CF_2CF_2)_nCH_2OH$ (n=12 at a maximum), can be produced by reacting methanol with tetrafluoroethylene in the presence of t-butyl octyl peroxide.

However, even if the telomer mixture obtained by this process is purified by distillation, the evaporation residue of the order of about a few hundreds of ppm cannot be eliminated, with the result that when it is used as a solvent in the manufacture of an information recording medium comprising a substrate and as built thereon a recording layer adapted for laser writing and/or reading, such as CD-R and DVD-R, for instance, the disadvantage is inevitable that the quality of the information recording medium is not high enough owing to the influence of said evaporation residue.

It is an object of the invention to provide a fluoroalcohol of the following general formula (1)

$$H(CFR^1CF_2)_nCH_2OH \quad (1)$$

(wherein n and R1 are as defined above), which is substantially free of impurities such as an evaporation residue and UV-absorbing substances, a method for producing said fluoroalcohol, use of said fluoroalcohol as a solvent for the manufacture of an information recording medium comprising a substrate and as built thereon a recording layer adapted for laser writing and/or reading, and an information recording medium comprising a substrate and as built thereon a recording layer adapted for laser writing and/or reading.

DISCLOSURE OF THE INVENTION

The invention relates to the following 1–20.

1. A method for producing a fluoroalcohol of the following formula (1):

$$H(CFR^1CF_2)_nCH_2OH \quad (1)$$

(wherein $R^1$ represents F or $CF_3$, when n=1; $R^1$ represents F, when n=2) comprising reacting methanol with tetrafluoroethylene or hexafluoropropylene in the presence of a free radical source, wherein the reaction mixture is subjected to distillation either in the presence of a base or after contact of said reaction mixture with a base.

2. The process for producing a fluoroalcohol as defined in claim 1 wherein the base is a substance having a pKb value of not more than 2.

3. The process for producing a fluoroalcohol as defined in claim 1 wherein the base is an alkali metal alkoxide or an alkali metal hydroxide.

4. The process for producing a fluoroalcohol as defined in claim 1 wherein the base is at least one selected from the group consisting of sodium alkoxides, sodium hydroxide and potassium hydroxide.

5. The process for producing a fluoroalcohol as defined in claim 1 wherein the fluoroalcohol of the formula (1)

$$H(CFR^1CF_2)_nCH_2OH \quad (1)$$

(wherein $R^1$ and n are as defined above) as obtained by distillation has an evaporation residue of not more than 50 ppm.

6. The process for producing a fluoroalcohol as defined in claim 5 wherein the fluoroalcohol of the formula (1)

$$H(CFR^1CF_2)_nCH_2OH \quad (1)$$

(wherein $R^1$ and n are as defined above) as obtained by distillation has an evaporation residue of not more than 25 ppm.

7. The process for producing a fluoroalcohol as defined in claim 5 wherein the fluoroalcohol of the formula (1)

$$H(CFR^1CF_2)_nCH_2OH \quad (1)$$

(wherein $R^1$ and n are as defined above) as obtained by distillation has an evaporation residue of not more than 10 ppm.

8. The process for producing a fluoroalcohol as defined in claim 1 wherein the free radical source is at least one selected from the group consisting of a reaction initiator, UV and heat.

9. The process for producing a fluoroalcohol as defined in claim 8 wherein the free radical source is a reaction initiator having an half-life at the reaction temperature of about 10 hours.

10. The process for producing a fluoroalcohol as defined in claim 8 wherein the free radical source is a peroxide.

11. The process for producing a fluoroalcohol as defined in claim 8 wherein the free radical source is di-t-butylperoxide, t-butylperoxyisopropylcarbonate or t-butylperoxy-2-ethylhexanoate.

12. The process for producing a fluoroalcohol as defined in claim 1 wherein an acid acceptor is used together with the free radical source.

13. A fluoroalcohol of the following formula (1)

$$H(CFR^1CF_2)_nCH_2OH \quad (1)$$

(wherein $R^1$ represents F or $CF_3$, when n=1; $R^1$ represents F, when n=2) which has an evaporation residue of not more than 50 ppm.

14. The fluoroalcohol according to claim 13, the evaporation residue of which is not more than 25 ppm.

15. The fluoroalcohol according to claim 13, the evaporation residue of which is not more than 10 ppm.

16. The fluoroalcohol according to claim 13, the absorbance (190–300 nm) in methanol of which is not more than 0.2 abs.

17. The fluoroalcohol according to claim 13, the absorbance (205 nm) in methanol of which is not more than 0.1 abs.

18. The fluoroalcohol according to claim 17, the absorbance (205 nm) in methanol of which is not more than −0.2 abs.

19. Use of the fluoroalcohol claimed in claim 13 for the manufacture of an information recording medium comprising a substrate and as built thereon a recording layer adapted for laser writing and/or reading.

20. An information recording medium comprising a substrate and as built thereon a recording layer adapted for laser writing and/or reading as fabricated using the fluoroalcohol of the following formula (1)

$$H(CFR^1CF_2)_nCH_2OH \qquad (1)$$

(wherein $R^1$ represents F or $CF_3$, when n=1; $R^1$ represents F, when n=2) as produced by the process as defined in claim 1 or the fluoroalcohol of the following formula (1)

$$H(CFR^1CF_2)_nCH_2OH \qquad (1)$$

(wherein $R^1$ represents F or $CF_3$, when n=1; $R^1$ represents F, when n=2) as defined in claim 13.

In the production process according to the invention, methanol is used in excess over tetrafluoroethylene or hexafluoropropylene. The reaction temperature is about 40–140° C., the reaction time is about 3–12 hours, and the reaction pressure is about 0.2–1.2 MPa. This reaction can be conducted in a high pressure reactor such as autoclave, for instance. The reaction system is preferably subjected to an inert gas purging using nitrogen, argon or the like gas.

Upon completion of the reaction, the excess methanol is optionally distilled off and the residue is further subjected to distillation in the presence of a base. Furthermore, in the event the reaction mixture contains $H(CF_2CF_2)_nCH_2OH$ (n≧3) or $H(CF(CF_3)CF_2)_nCH_2OH$ (n≧2) as impurity, the impurity is preferably removed in advance by distillation. The reaction mixture containing the fluoroalcohol of the formula (1)

$$H(CFR^1CF_2)_nCH_2OH \qquad (1)$$

(wherein n and $R^1$ are as defined above) is subjected to distillation either in the presence of a base or after contacting the reaction mixture with a base.

The base to be added to the above reaction mixture or contacted therewith is preferably a base with a pKb value of not more than 2, thus including alkali metal alkoxides such as sodium methoxide, sodium ethoxide, sodium propoxide, potassium t-butoxide, lithium ethoxide, etc., alkali metal hydroxides such as sodium hydroxide, potassium hydroxide, lithium hydroxide, etc., calcium hydroxide, aluminum hydroxide, barium hydroxide, magnesium hydroxide and soda lime. The proportion of the base is about 0.05–1.0 mole, preferably about 0.1–0.5 mole, per 1 kg of the reaction mixture from which methanol has been removed.

The acid acceptor includes but is not limited to the carbonates and hydrogencarbonates of alkali metals or alkaline earth metals, such as calcium carbonate, magnesium carbonate, barium carbonate, sodium carbonate, potassium carbonate, sodium hydrogencarbonate, potassium hydrogencarbonate and the like, calcium oxide, calcium hydroxide and soda lime. The preferred acid acceptor is a substance capable of capturing the acid generated during reaction, e.g. HF, without imparting strong basicity to the reaction system.

The amount of the acid acceptor is not specifically limited to, but may be about 0.001–0.1 mole based on 1 mole of tetrafluoroethylene or hexafluoropropylene.

As the free radical source or generator, at least one member selected from the group consisting of a reaction initiator, UV and heat can be used. When the free radical source is UV, the UV light from a medium-pressure or high-pressure mercury lamp, for instance, can be selected. When the free radical source is heat, a temperature between 250 and 300° C., for instance, can be selected. The reaction initiator includes but is not limited to peroxides and it is preferable to use an initiator with a half-life of about 10 hours at the reaction temperature.

The preferred free radical source includes perbutyl D (di-t-butylperoxide), perbutyl O (t-butylperoxy-2-ethylhexanoate) and perbutyl I (t-butylperoxyisopropylcarbonate). The amount of the reaction initiator should generally be about 0.005~0.1 mole based on 1 mole of tetrafluoroethylene or hexafluoropropylene.

The amount of the evaporation residue in the fluoroalcohol obtained in accordance with the invention is 50 ppm or less, preferably 25 ppm or less, more preferably 10 ppm or less.

The amount of the evaporation residue can be determined as follows. Thus, the fluoroalcohol is evaporated at 40° C. and 5 mmHg and the residue is weighed and expressed in mass ppm based on the fluoroalcohol such as $HCF_2CF_2CH_2OH$.

The UV absorbance in methanol at 205 nm of the fluoroalcohol of general formula (1) as obtained in accordance with the invention is not greater than 0.1 abs, preferably –0.1 abs or less, more preferably –0.2 abs or less. The UV absorbance in methanol can be measured using a mixture of 1 ml of the fluoroalcohol of general formula (1) and 3 ml of methanol as a sample and methanol as a reference.

That the fluoroalcohol according to the invention is "substantially free of impurity" means that (i) the residue on distillation of the fluoroalcohol is not more than 50 ppm, preferably not more than 25 ppm, more preferably not more than 10 ppm and/or (ii) the UV absorbance (205 nm) thereof in methanol is not more than 0.1 abs, preferably not more than –0.1 abs, more preferably not more than –0.2 abs.

The information recording medium comprising a substrate and as built thereon a recording layer adapted for laser writing and/or reading can be manufactured by dissolving a dye in a solvent containing the fluoroalcohol of general formula (1) according to the invention, preferably a fluorine-series solvent containing said fluoroalcohol, followed by carrying out the routine series of operations, using the resulting dye solution, inclusive of coating a substrate with it and drying the coated substrate to provide a dye-containing recording layer. The dye mentioned above includes cyanine dyes, phthalocyanine dyes, pyrylium dyes, thiopyrylium dyes, squarylium dyes, azulenium dyes, indophenol dyes, indoaniline dyes, triphenylmethane dyes, quinone dyes, aminium dyes, diimmonium dyes, and metal complex dyes. The raw material for the substrate includes plastics such as polycarbonates, poly(methyl methacrylate), epoxy resin, amorphous polyolefins, polyesters, poly(vinyl chloride), etc., glass and ceramics. For the purpose of improving surface smoothness and adhesion or preventing degradation of the recording layer, a primer coating or an undercoat may be provided between the recording layer and the substrate and/or a protective layer may be formed on the recording layer.

In accordance with the invention, there can be easily provided substantially impurity-free $HCF_2CF_2CH_2OH$, $H(CF_2CF_2)_2CH_2OH$ and $HCF(CF_3)CF_2CH_2OH$ which are suited for use in the manufacture of an information recording medium comprising a substrate and as built thereon a recording layer adapted for laser writing and/or reading (optical disks such as CD-R, DVD-R, etc.) or photosensitive material for film.

BEST MODE FOR CARRYING OUT THE INVENTION

The following examples illustrate the invention in further detail.

EXAMPLE 1

Methanol (2 L), di-t-butylperoxide (45 g) and calcium carbonate (30 g) were added to an autoclave. After nitrogen purging, tetrafluoroethylene was introduced into the autoclave at an initial rate of 600 g/hr. With controlling the temperature and pressure at 125° C. and 0.8 MPa, respectively, the reaction was carried out for 6 hours.

After cooling, the reaction mixture was distilled to remove methanol and then $H(CF_2CF_2)_nCH_2OH$ (n is an integer of 2 or more) to give a fraction of $HCF_2CF_2CH_2OH$ (1.2 L). The evaporation residue of the $HCF_2CF_2CH_2OH$ fraction was approximately 600 ppm and the absorbance (205 nm) thereof was 2.0 abs. Capillary GC/MS analysis revealed various aldehydes such as HCHO, $HCF_2CF_2CHO$, $HCF_2CHFCHO$, $HCF_2CF_2CF_2CF_2CHO$, $HCF_2COOCH_2CH=CHCHO$, $HCF_2CH_2COOCH=CHCHO$, $HCF_2CF_2CH(OH)OCH_2CHO$ as impurity.

Repeated distillation of the above fraction caused little change in any of the amount of said impurity, evaporation residue and absorbance (205 nm).

To the $HCF_2CF_2CH_2OH$ fraction obtained above (1 L) was added 28% sodium methoxide in methanol (30 g), and the mixture was distilled under heating to give $HCF_2CF_2CH_2OH$ which was substantially free of impurity. The distillation residue of the $HCF_2CF_2CH_2OH$ thus obtained was not more than 10 ppm and the absorbance (205 nm) thereof was not more than −0.2 abs. The amount of the aldehydes mentioned above was below the detection limit of GC/MS.

The conditions of GS/MS analysis were as follows.
1)
Column: Liquid phase DB-1301
Film thickness: 1.00 μm
Column size: 60 m×0.247 mm
2) Conditions of Analysis
Carrier He: 200 kPa
Air: 40 kPa
H2: 50 kPa
Temperature: 50° C. for 5 min to 220° C. for 15 min (the temperature was elevated at the rate of 15° C./min)
Injection: 200° C.

EXAMPLE 2

The $H(CF_2CF_2)_nCH_2OH$ (n≧2) fraction was subjected to fractional distillation to recover an $H(CF_2CF_2)_2CH_2OH$ fraction. To this fraction was added sodium methoxide as shown in Example 1, and the mixture was distilled to give an $H(CF_2CF_2)_2CH_2OH$ fraction showing an evaporation residue of not more than 25 ppm.

EXAMPLE 3

Except that hexafluoropropylene was used in place of tetrafluoroethylene, the reaction and the distillation procedure for purification were carried out in the same manner as in Example 1. As a result, $HCF(CF_3)CF_2CH_2OH$ having an evaporation residue of not more than 25 ppm and an UV absorbance (205 nm) of not more than 0.1 abs was obtained.

EXAMPLE 4

The $HCF_2CF_2CH_2OH$ fraction prior to distillation in the presence of a base as obtained in Example 1 was passed through a column of soda lime to remove HF. As a result, the gas chromatographic purity dropped from 99.974% to 99.5368%.

When this $HCF_2CF_2CH_2OH$ fraction of decreased purity was distilled, $HCF_2CF_2CH_2OH$ giving an evaporation residue of not more than 50 ppm and an UV absorbance (205 nm) value of not more than 0.1 abs was obtained.

What is claimed is:

1. A method for producing a fluoroalcohol of the following formula (1):

$$H(CFR^1CF_2)_nCH_2OH \qquad (1)$$

(wherein $R^1$ represents F or $CF_3$, when n=1; $R^1$ represents F, when n=2) having an evaporation residue of not more than 50 ppm for the manufacture of an information recording medium comprising reacting methanol with tetrafluoroethylene or hexafluoropropylene in the presence of a free radical source, wherein the reaction mixture is subjected to distillation either in the presence of a base or after contact of said reaction mixture after completion of the reaction with a base.

2. The process for producing a fluoroalcohol as defined in claim 1 wherein the base is a substance having a pKb value of not more than 2.

3. The process for producing a fluoroalcohol as defined in claim 1 wherein the base is an alkali metal alkoxide or an alkali metal hydroxide.

4. The process for producing a fluoroalcohol as defined in claim 1 wherein the base is at least one selected from the group consisting of sodium alkoxides, sodium hydroxide and potassium hydroxide.

5. The process for producing a fluoroalcohol as defined in claim 1 wherein the fluoroalcohol of the formula (1)

$$H(CFR^1CF_2)_nCH_2OH \qquad (1)$$

(wherein $R^1$ and n are as defined above) as obtained by distillation has an evaporation residue of not more than 50 ppm.

6. The process for producing a fluoroalcohol as defined in claim 5 wherein the fluoroalcohol of the formula (1)

$$H(CFR^1CF_2)_nCH_2OH \qquad (1)$$

(wherein $R^1$ and n are as defined above) as obtained by distillation has an evaporation residue of not more than 25 ppm.

7. The process for producing a fluoroalcohol as defined in claim 5 wherein the fluoroalcohol of the formula (1)

$$H(CFR^1CF_2)_nCH_2OH \qquad (1)$$

(wherein $R^1$ and n are as defined above) as obtained by distillation has an evaporation residue of not more than 10 ppm.

8. The process for producing a fluoroalcohol as defined in claim 1 wherein the free radical source is at least one selected from the group consisting of a reaction initiator, UV and heat.

9. The process for producing a fluoroalcohol as defined in claim 8 wherein the free radical source is a reaction initiator having an half-life at the reaction temperature of about 10 hours.

10. The process for producing a fluoroalcohol as defined in claim 8 wherein the free radical source is a peroxide.

11. The process for producing a fluoroalcohol as defined in claim 8 wherein the free radical source is di-t-butylperoxide, t-butylperoxyisopropylcarbonate or t-butylperoxy-2-ethylhexanoate.

12. The process for producing a fluoroalcohol as defined in claim 1 wherein an acid acceptor is used together with the free radical source.

13. A fluoroalcohol of the following formula (1):

$$H(CFR^1CF_2)_nCH_2OH \quad (1)$$

(wherein $R^1$ represents F or $CF_3$, when n=1; $R^1$ represents F, when n=2) for the manufacture of an information recording medium which has an evaporation residue of not more than 50 ppm.

14. The fluoroalcohol according to claim 13, the evaporation residue of which is not more than 25 ppm.

15. The fluoroalcohol according to claim 13, the evaporation residue of which is not more than 10 ppm.

16. The fluoroalcohol according to claim 13, the absorbance (190–300 nm) in methanol of which is not more than 0.2 abs.

17. The fluoroalcohol according to claim 13, the absorbance (205 nm) in methanol of which is not more than 0.1 abs.

18. The fluoroalcohol according to claim 17, the absorbance (205 nm) in methanol of which is not more than −0.2 abs.

19. A method of using the fluoroalcohol claimed in claim 13 for the manufacture of an information recording medium comprising: obtaining a substrate; and building on said substrate a recording layer adapted for laser writing or reading.

20. An information recording medium comprising a substrate and as built thereon a recording layer adapted for laser writing and/or reading as fabricated using the fluoroalcohol of the following formula (1)

$$H(CFR^1CF_2)_nCH^2OH \quad (1)$$

(wherein $R^1$ represents F or $CF_3$, when n=1; $R^1$ represent F, when n=2) as produced by the process as defined in claim 1 or the fluoroalcohol of the following formula (1)

$$H(CFR^1CF_2)_2CH^2OH \quad (1)$$

(wherein $R^1$ represents F or $CF_3$, when n=1; $R^1$ represent F, when n=2) as produced by the process as defined in claim 1 or the fluoroalcohol of the following formula (1) which has an evaporation residue of not more than 50 ppm.

* * * * *